United States Patent
Hu et al.

(10) Patent No.: US 10,406,198 B2
(45) Date of Patent: Sep. 10, 2019

(54) METHODS FOR MAKING CONJUGATES FROM DISULFIDE-CONTAINING PROTEINS

(71) Applicant: NOVARTIS AG, Basel (CH)

(72) Inventors: Qi-Ying Hu, Needham, MA (US); Martin Allan, Cambridge, MA (US)

(73) Assignee: Novartis AG, Basel (CH)

(*) Notice: Subject to any disclaimer, the term of this patent is extended or adjusted under 35 U.S.C. 154(b) by 338 days.

(21) Appl. No.: 15/312,267

(22) PCT Filed: May 22, 2015

(86) PCT No.: PCT/US2015/032126
§ 371 (c)(1),
(2) Date: Nov. 18, 2016

(87) PCT Pub. No.: WO2015/179734
PCT Pub. Date: Nov. 26, 2015

(65) Prior Publication Data
US 2017/0095572 A1    Apr. 6, 2017

Related U.S. Application Data

(60) Provisional application No. 62/002,585, filed on May 23, 2014.

(51) Int. Cl.
*A61K 9/00* (2006.01)
*A61K 38/05* (2006.01)
*A61K 47/68* (2017.01)

(52) U.S. Cl.
CPC .............. *A61K 38/05* (2013.01); *A61K 47/68* (2017.08); *A61K 47/6803* (2017.08); *A61K 47/6849* (2017.08); *A61K 47/6855* (2017.08)

(58) Field of Classification Search
CPC ...................................................... A61K 38/05
See application file for complete search history.

(56) References Cited

FOREIGN PATENT DOCUMENTS

| WO | WO 96/41813 A2 | 12/1996 |
|----|----|----|
| WO | WO 2013/111110 A2 | 8/2013 |
| WO | WO 2013/132268 A1 | 9/2013 |
| WO | WO 2013/190292 A2 | 12/2013 |

(Continued)

OTHER PUBLICATIONS

McReynolds et al., "Synthesis of Hydrophilic Aminooxy Linkers and Multivalent Cores for Chemoselective Aldehyde/Ketone Conjugation," Tetrahedron Lett. 2014; 55(14):2270-2273.

(Continued)

*Primary Examiner* — Paul W Dickinson
(74) *Attorney, Agent, or Firm* — Daniel A. Raymond; Genomics Institute of the Novartis Research Foundation

(57) ABSTRACT

The invention provides methods to prepare protein conjugates from proteins having at least four accessible cysteine residues. In one embodiment, an antibody with four reducible disulfide linkages is reduced to provide four pairs of free cysteines. Each pair of free cysteines is reacted with a 1,3-dihaloacetone or similar reactant, linking the sulfur atoms of each pair together though a 3-carbon tether with a reactive ketone. A pair of these reactive ketones are linked together with and used to attach a single payload molecule, thus conjugating the antibody to two payload groups. This method gives a stabilized antibody conjugate with high selectivity for a ratio of two payloads per antibody.

13 Claims, 7 Drawing Sheets

Protein → Reduced Protein → Activated Protein

Activated Protein → H₂N-X-L-PL → Protein Conjugate

(56) References Cited

FOREIGN PATENT DOCUMENTS

WO    WO 2014/083505 A1    6/2014

OTHER PUBLICATIONS

Berthelmann et al., "Versatile C3-symmetric scaffolds and their use for covalent stabilization of the foldon trimer," Org. Biomol. Chem. 2014; 12(16):2606-14.

Khomutov et al., "Synthesis of hydroxylamine analogues of polyamines", Tetrahedron. 1996; 52(43):13751-13766.

International Search Report and Written Opinion for International Application No. PCT/US2015/032126, dated Sep. 1, 2015 (11 pages).

Figure 2. Antibody general structure showing inter-chain disulfides.
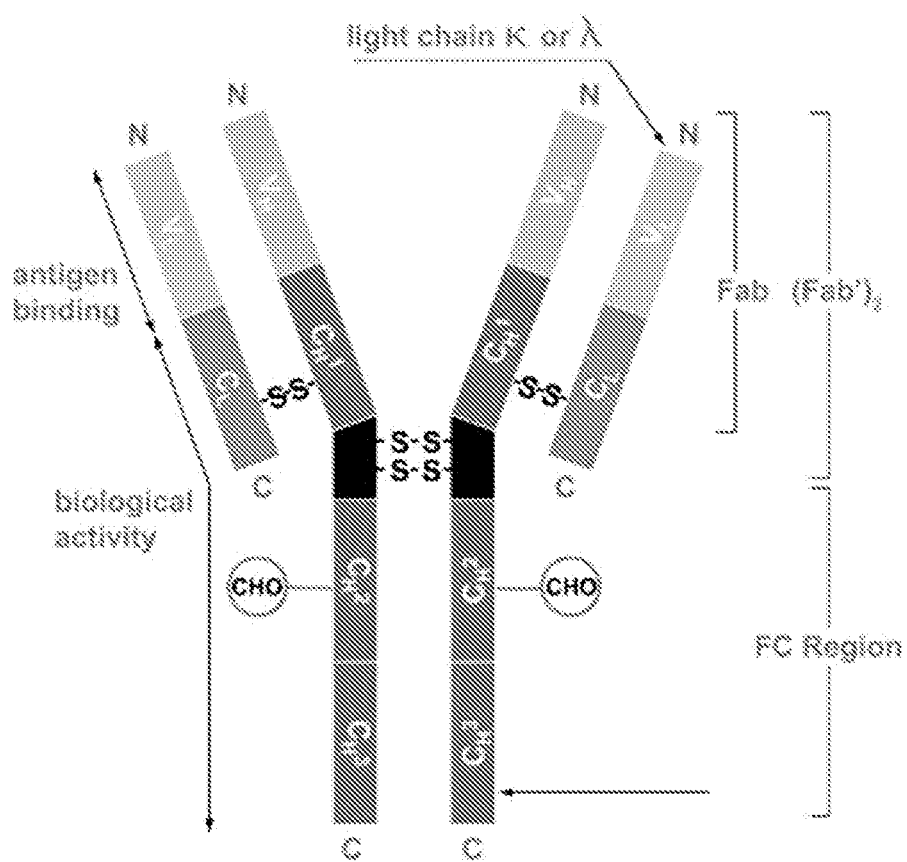

SDS-PAGE of Fc, 12 and 14

1. 14
2. 12
3. Fc

SDS-PAGE of trastuzumab and trastuzumab-diazido 1. (another trastuzumab conjugate)
2. Trastuzumab-diazido
3. Trastuzumab
   (1R, 2R and 3R are reduced samples)

1. 17
2. 16
3. anti-Her2 IgG (1R, 2R and 3R are 17, 16, anti-Her2 IgG pretreated with excess reducing reagents)

METHODS FOR MAKING CONJUGATES FROM DISULFIDE-CONTAINING PROTEINS

BACKGROUND

A wide variety of chemical moieties ('payloads') have been covalently attached to enzymes, antibodies, and other polypeptides or proteins, to form conjugates. The payloads may be used to locate the protein to which they are attached (e.g., labels), to modify the physicochemical properties or stability of the protein (e.g., PEGylation), to enable the protein to be attached to another molecule or protein (functional or coupling groups, for connecting the conjugate to another compound or another conjugate), or to modify the function or activity of the payload or the protein (e.g., vaccine conjugates). The protein may also act as a carrier to deliver the attached payload to a particular tissue or cell type, such as in antibody-drug conjugates (ADCs). Classes of payloads that can be usefully linked to proteins include detectable moieties (labels), anchoring moieties to attach the protein to a surface or another compound, antigens that elicit an immune response when conjugated to a protein, coupling groups that react readily with a chemically complementary coupling partner (thus connecting the protein to another entity), and therapeutic moieties such as cytotoxins and other bioactive agents.

Attaching these diverse structures to proteins in a controlled and reproducible fashion is often critical for the conjugates to function correctly, particularly when they are used as therapeutic agents. In ADCs, for example, it is important to carefully control the number of payload compounds attached to an antibody, which is not easy since the carrier is a large and complex protein. For example, depending on the particular target, linker, and cytotoxin, the optimum DAR (drug to antibody ratio) for an ADC may vary from 1 to 6 or more, in order to balance factors such as efficacy, stability, and safety. If ADCs are made as mixtures with varying drug/antibody ratios (DARs), separation is difficult, and consistency of the product is important for both therapeutic and regulatory reasons. Thus there is a need for methods to produce ADCs with good control of drug-antibody ratios, as well as efficient conjugation and consistent placement of the payload attachment point.

A number of methods have been developed for attaching payloads to proteins to address some of these issues. See, e.g., Sletten, E. M. and Bertozzi, C. R. *Angew. Chem. Int. Ed.* 2009, 48, 6974-6998; Basle', E.; Joubert, N.; Pucheault, M. *Chemistry & Biology* 2010, 17, 213-227; and Hermanson, G. T. *Bioconjugate Techniques*, 2nd ed.; Academic Press: San Diego, Calif., 2008. The most common conjugation methods rely on the chemical reactivity of certain amino acids that occur naturally in many natural proteins: lysine and cysteine are often used, because they provide a reactive site for connecting the payload to the protein. Proteins often have more lysines than the optimum number of payloads to be attached, though: adding enough payload moieties to occupy all of the availably lysines in order to produce a consistent, homogenous product may add too many payload molecules for optimum efficacy, while partial loading typically provides a heterogeneous product, which can be problematic for a variety of reasons—in the case of Mylotarg™, the first commercialized ADC, for example, the heterogeneity of the ADC product seems likely to have contributed to the issues that led to a decision to withdraw the product from registration. Fuenmayor, et al., *Cancers*, vol. 3, 3370-93 (2011).

The frequency of occurrence of cysteine in natural proteins is lower than that of lysine, and cysteine may be suitable for use as a site for conjugation where it is available in adequate numbers; where too few cysteines are present, one or more may be inserted by standard protein modification methods. However, it is often preferable to avoid modifying the sequence of the natural protein by inserting a cysteine or by removing a disulfide. While it is not difficult to convert a disulfide into two free cysteines by reducing the disulfide, doing so may disrupt the secondary or tertiary structure of the protein.

Some methods for inserting a tether between cysteine residues formed by reducing a disulfide on a protein have been reported. This approach is particularly appealing for ADC production, because the typical antibody structure contains four reducible inter-chain disulfides that can be utilized without protein engineering. One method used for such conjugation involves a sulfone-substituted methacrylate derivative. US2006/0210526. This method forms a reactive intermediate that requires an elimination step before alkylation of the second sulfur atom occurs. The conditions for that multi-step process can result in incomplete formation of a linker (tether) between cysteines, and the reaction conditions can cause protein denaturation. Another approach uses a maleimide derivative, e.g., a 3,4-dibromomaleimide. WO2011/018613. However, the conjugate formed in this process can suffer from stability problems because the Michael addition of the thiols on the maleimide ring is reversible, so the tether between the sulfur atoms or the payload itself can be lost. Thus novel methods are needed that turn disulfide groups into conjugation sites without giving up the stabilizing effect of the inter-chain disulfides, while also providing efficient conjugation, stability, and consistent payload/protein ratios. The present invention provides useful methods for making such ADCs.

SUMMARY

In one aspect, the invention provides a method to use two disulfides on an antibody to link a payload to the protein, forming a protein conjugate. The method involves reducing the disulfides to provide free thiol groups, and tying two thiol groups together with a bridging group that keeps them in about the same positions they occupied when they formed a disulfide. Keeping the cysteine groups in their same approximate positions minimizes any adverse effect on the protein's conformation that may occur upon reduction of the disulfide. The tether that is introduced to link the two thiol groups together contains a reactive functional group that can be used to attach a payload of interest. In some embodiments, the tether contains a carbonyl group that is reactive enough to form an oxime linkage with a hydroxylamine group, and the payload is conjugated to the activated protein by forming such linkage. For example, the reduced protein can be reacted with a 1,3-dihalo acetone such as dichloroacetone or dibromoacetone, thereby inserting a 3-carbon tether connecting the two sulfur atoms together. This may suitably simulate the effect of the disulfide, keeping the protein in a conformation very similar to the one it had when the disulfide was present, while it also provides greater stability than the disulfide as well as a place to attach a payload. The tethers used in the methods and compositions of the invention provide a chemically reactive functional group, and a protein containing this type of tether between two cysteine sulfur atoms is referred to herein as an activated protein. While each ketone can be used to attach a payload, in the present invention two such ketones or other tethering groups are connected together with a bridging group that provides a new point of attachment for a payload. As a result of using two S—S tethers to attach a bridging group that carries one payload, the number of payload compounds on a given polypeptide is one-half of the number of disulfides used in the conjugation method. The Figures herein provide a schematic representation of the conjugates of the invention. Other methods of using disulfides to form conjugates are described in WO/2014/083505 and PCT/IB2014/066300. The entire contents of WO/2014/083505 and PCT/IB2014/066300 and their priority documents are expressly incorporated herein by reference for all purposes.

These methods can be applied to any protein having two or more accessible disulfide linkages, and are typically useful for natural proteins having a molecular weight above 500 Da and typically above 2,000 Da, where a disulfide is present in the native or active form of the protein. The methods can be used with proteins containing more than one disulfide, such as 2-10, or typically up to 6 disulfide groups, at least two of which are sufficiently accessible to be reduced by conventional disulfide reducing agents.

These methods produce a conjugate containing at least one payload for each pair of disulfide groups that are utilized, and the conjugate substantially retains the native or active conformation of the protein.

BRIEF DESCRIPTION OF THE DRAWINGS

FIG. 2 provides a diagram of a generic antibody, illustrating the presence and position of the inter-chain disulfides that can be used in the methods of the invention for forming conjugates.

DETAILED DESCRIPTION OF EMBODIMENTS OF THE INVENTION

'Protein' and polypeptide as used herein refer to peptides containing ten or more amino acid residues connected by amide (peptide) bonds. A protein or polypeptide may be a single continuous strand or it may include two or more strands that associate naturally to form a stable complex, and may be or comprise a cyclic polypeptide. Typically the proteins described herein comprise mainly or only naturally occurring amino acids, though the methods described herein are equally useful with polypeptides that contain one or more non-natural amino acids. Commonly (but not necessarily) the amino acids are mostly or entirely of the L configuration and are selected from the common 'essential' amino acids. The methods are also suitable for use with polypeptide complexes that contain two or more peptide chains, where the disulfide bonds used for the methods of the invention may be inter-chain or intra-chain disulfides.

Figure 3A:
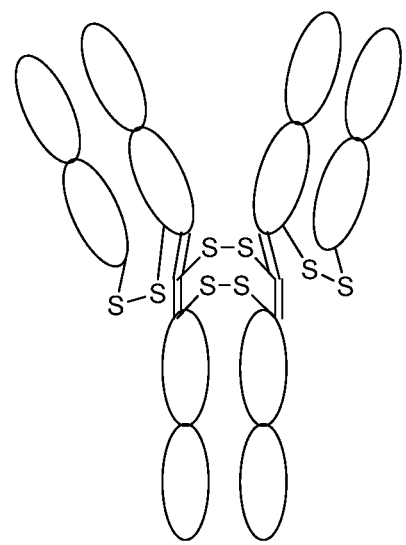
FIGS. 3A, 3B and 3C represent the subunits of an antibody with disulfides that are then used to make an activated polypeptide, and a polypeptide-payload conjugate of the invention.
Figure 3B:
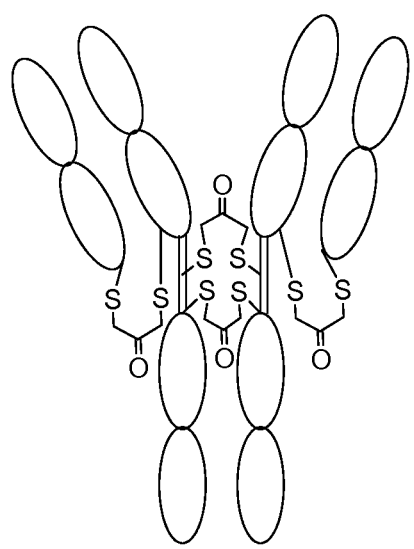
Figure 3C:
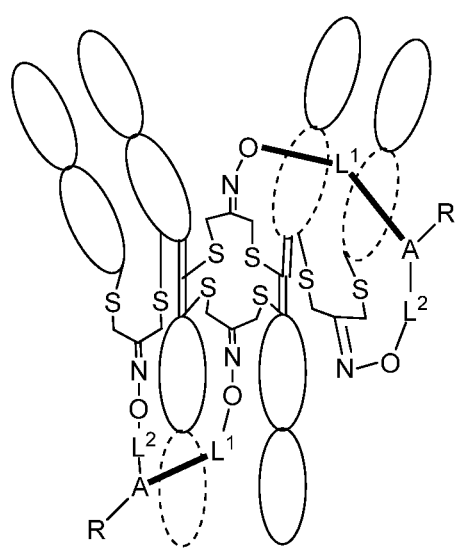

Abbreviations
DCM Dichloromethane
DIC Diisopropyl Carbodiimide
DIPEA Diisopropyl Ethyl Amine
EDT Ethane dithiol
HBTU N,N,N',N'-Tetramethyl-O-(1H-benzotriazol-1-yl)uronium hexafluorophosphate
MeCN acetonitrile
NMP N-methyl pyrrolidinone
PBS Phosphate-buffered saline
TCEP Tris(carboxyethyl)phosphine
TFA Trifluoroacetic acid
TIPS Triisopropyl silane An example of one embodiment of the invention is shown in FIGS. 3A-3C. The Figure depicts a generic antibody schematically, showing four inter-chain disulfide bonds. In one embodiment the inter-chain disulfides are all reduced, forming a reduced protein having eight free thiols derived from the disulfides. The reduced polypeptide is then allowed to react with a dihaloacetone or similar bis-electrophile (e.g., 1,3-dichloroacetone or 1,3-dibromoacetone) to form an activated protein wherein each pair of thiols is linked together through a functionalized tether: the tether in this example contains a free ketone group that is reactive toward Schiff base formation. A bis-alkoxyamine bridging group is then allowed to react with the ketones of the activated polypeptide, wherein a single payload group is attached to the bridging group.

The methods of the invention can also be used with other tethering groups between sulfur atoms from a disulfide. For example, methods to tie together sulfhydryl groups using cyclic groups are known in the art, using dibromomaleimide with a payload attached to the ring nitrogen. These can be adapted to produce conjugates of the invention by tying to of the linker moieties together to form a bridge that carries one payload compound, as depicted here. This double-attachment should also reduce potential problems caused by reversible Michael addition of S onto the maleimide ring, which can release the payload (cytotoxin) prematurely. In the conjugate attached at four sulfur atoms, the risk of premature release of payload should be reduced.

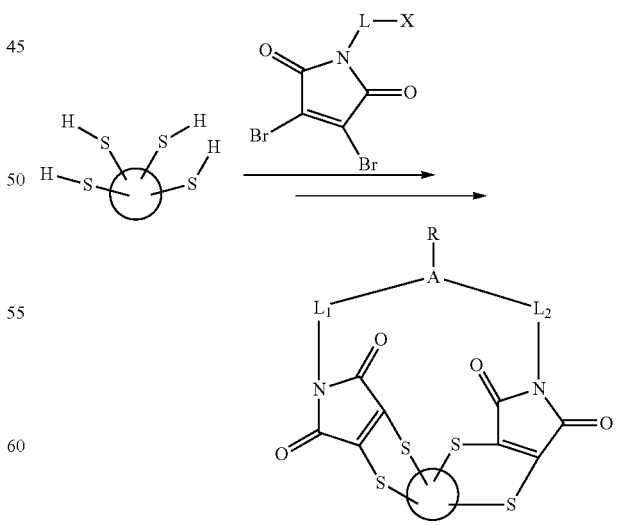

Similarly, methods for using a pair of sulfur atoms to link a payload by Michael addition/elimination from a substituted methacrylate are known in the art, and can be adapted to provide conjugates of the invention. Instead of linking one payload through the carboxylate of a methacrylate, two methacrylate groups can be bridged together either before or after conjugation to the protein as shown here.

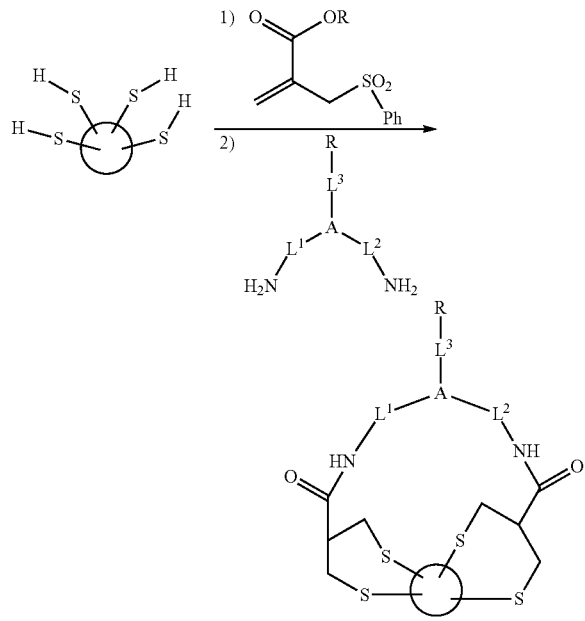

The methods of the invention are suitable for use to form conjugates from most polypeptides that contain at least two disulfide linkages that can be reduced without denaturing the protein, or that contain four or more free cysteine residues that can be connected in pairs by reaction with a 1,3-dihaloacetone reactant. Typically, the polypeptide is one where the thiols react with dichloroacetone or dibromoacetone under conditions described herein to produce at least 50% cross-linking of the two thiols, and frequently the extent of cross-linking is at least about 70%, 80% or 90%.

A pair of cysteines to be linked together may be on a single polypeptide strand, or they may be on separate polypeptide strands that form a polypeptide complex. In certain embodiments, the methods utilize a protein or polypeptide having 2-6 disulfide linkages, or 4-8 free cysteine residues, and involve reduction of at least two of the disulfides. The disulfide-containing polypeptide can be any polypeptide having at least 10 amino acid residues, preferably at least 50 amino acids, that contains a pair of disulfide linkages within a single polypeptide sequence, including a polypeptide complex where a disulfide (or two or more disulfides) connects one polypeptide sequence to another amino acid or polypeptide, provided the complex does not dissociate rapidly when the disulfides are reduced for insertion of the tether between the sulfur atoms. Typical proteins for use in the methods of the invention include cyclic peptides and linear peptides containing about 50 to about 5000 amino acids, typically at least 100 amino acids and up to about 2000, including functional proteins such as enzymes or receptors; protein complexes having at least two disulfide linkages (often connecting two separate polypeptide strands); structural proteins; proteins used as vaccine scaffolds such as CRM197 or other proteins having adjuvant activity; and particularly antibodies or antibody fragments having at least two reducible disulfide bonds, e.g., Fc. Particularly useful proteins for these methods include antibodies, especially monoclonal antibodies including engineered antibodies, modified antibodies and antibody fragments having two inter-chain disulfides; vaccine carrier proteins such as CRM197; and single-stranded proteins having at least two disulfide linkages or at least four cysteine residues and having a molecular weight between 500 and 500,000, typically between 1,000 and 200,000. Methods for engineering an antibody or other protein to introduce two or more cysteine residues, for example, and for modifying antibodies are well known in the art.

The methods are especially useful with antibodies and antibody subunits containing at least two reducible disulfides, including IgG and Fc, which have two to four accessible inter-strand disulfide bonds that are readily reduced by methods known in the art.

The disulfide linkages of disulfide-containing proteins for use in the methods and compositions of the invention are reduced to form four or more free thiol groups: methods for such reduction are well known in the art. In some embodiments, the reduction is performed using a reducing agent that selectively reduces disulfide linkages that are readily accessible to solvent around the protein: one suitable reducing agent is tris(2-carboxyethyl)phosphine (TCEP) and its salts—see *Analytical Biochemistry* 273, 73-80 (1999). Other known disulfide-reducing agents such as dithiothreitol, 2-mercaptoethanol, cysteamine, and dithiobutylamine (J M Perkel, *Chem. Eng'g News*, Feb. 29, 2012; Lukesh, et al., *J. Am. Chem. Soc.*, 134, 4057-59 (2012)) and trialkyl phosphines such as tributyl phosphine (WO2008/157380) can also be used.

The linking groups $L^1$, $L^2$ and $L^3$ can be any suitable organic linkages that connect $T^1$ and $T^2$ to A, and connect A to the payload R. Suitable examples of $L^1$ and $L^2$, which may be the same or different, include [T]-$(CH_2)_{1-6}$-[A]; [T]-$(CH_2)_{1-6}C(=O)$-[A]; [T]-$(CH_2)_{1-6}C(=O)$—NH-[A]; [T]-$CH_2C(=O)$—O-[A]; [T]-$(CH_2CH_2O)_n$-[A]; [T]-Phenyl-C(O)NH-[A], and combinations of these, where n is typically 1-20, and [T] and [A] respectively indicate which end of the linker is attached to group $T^1$ or $T^2$, and which end connects to group A. Some examples of suitable linkages for $L^3$ include [A]-C(=O)—$(CH_2)_{1-6}$—[R]; [A]-$CH_2C(=O)$—[R]; [A]-$CH_2C(=O)$—NH—[R]; [A]-$CH_2C(=O)$—O—[R]; [A]-$(CH_2CH_2O)_n$—[R]; [A]-Phenyl-C(O)NH—[R], and the like, where n is typically 1-20, and [A] and [R] respectively indicate which end of the linker is attached to group A, and which end connects to payload R. In some embodiments, the linker $L^3$ can have two payloads attached to increase payload loading on the conjugate. In other embodiments, the linker $L^3$ can have three payloads attached to increase payload loading on the conjugate. Where more than one payload is attached to a given linker the payloads can be the same or different. Suitable linkers also include combinations of the components of these groups: the nature of the linkers is not critical to the practice of the invention and can be based on convenience and availability of methods for attachment to at least one payload R, or on desired physicochemical properties for the conjugate, or on its intended use. Selection of suitable linkers is within the level of ordinary skill and depends on the structure of the Payload R and available methods for modifying it to attach linker $L^3$ as well as whether the planned use makes it desirable to use a cleavable linker. Typically the linker is attached at one or both ends via an amide or ester group; frequently the linker L contains a peptide bond or ester to allow in vivo lysis by protease or esterase activities (for example val-cit, a dipeptide that is cleaved by cathepsin B, or Gly-phe-leu-gly, which is also cleavable by cathepsin B); optionally it contains one or more ethylene oxide units (—OCH$_2$CH$_2$—); and in many embodiments it contains at least one and up to six amino acid moieties. Suitable embodiments of linkers L$^1$, L$^2$ and L$^3$ may also comprise one or more components selected from the following groups:

(a) a bond, —O—, —S—, —S—S—, —NH—, —N((C$_1$-C$_6$)alkyl)-, —NH—C(O)—NH—, —C(O)—NH—, —NH—C(O)—;

(b) (C$_1$-C$_{20}$)alkylene, (C$_2$-C$_{20}$)alkenylene, (C$_2$-C$_{20}$)alkynylene, —Z—(C$_1$-C$_{20}$)alkylene-, —Z—(C$_2$-C$_{20}$)alkenylene, —Z—(C$_2$-C$_{20}$)alkynylene, (C$_1$-C$_{20}$)alkylene-Z—(C$_1$-C$_{20}$)alkylene, (C$_2$-C$_{20}$)alkenylene-Z—(C$_2$-C$_{20}$)alkenylene, (C$_2$-C$_{20}$)alkynylene-Z—(C$_2$-C$_{20}$)alkynylene, where Z is —C(O)—, —NH—, —N(C$_1$-C$_6$)alkyl)-, —NH—C(O)—NH—, —C(O)—NH—, —NH—C(O)—, (C$_3$-C$_7$)cycloalkylene, phenylene, heteroarylene, or heterocyclene and where said (C$_1$-C$_{20}$)alkylene, said (C$_2$-C$_{20}$)alkenylene, and said (C$_2$-C$_{20}$)alkynylene moieties each independently optionally contain one or more oxygen atoms interdispersed within said moieties, such that the oxygen atoms are separated by at least one and preferably two carbon atoms;

(c) (C$_3$-C$_7$)cycloalkylene, (C$_3$-C$_7$)cycloalkylene-Y—(C$_3$-C$_7$)cycloalkylene, —Y—(C$_3$-C$_7$)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is (C$_1$-C$_{20}$)alkylene, (C$_2$-C$_{20}$)alkenylene, (C$_2$-C$_{20}$)alkynylene, —O—, —C(O)—, —S—, —NH—, —N((C$_1$-C$_6$)alkyl)-, —NH—C(O)—NH—, —C(O)—NH—, or —NH—C(O)— and where said (C$_3$-C$_7$)cycloalkylene, said phenylene, said heteroarylene, and said heterocyclene moieties are each individually optionally substituted with 1 to 3 substituents selected from halo, (C$_1$-C$_4$)alkyl or halo-substituted (C$_1$-C$_4$)alkyl;

(d) —[OCH$_2$CH$_2$]$_v$—, where v is 1-20, preferably 1-10; and (e) a peptide comprising 1 to 100 amino acids, preferably 1-30 or 1-6 amino acids.

Furthermore, L$^3$ can be or can comprise a cleavable linker such as Val-Cit (valine-citrulline, a dipeptide that is selectively cleaved by cathepsin B), or val-cit-PABC (valine-citrulline p-aminobenzylcarbamate, see *Bioconjugate Chem.* 19(10), 1960-63 (2008)), a disulfide, or a linker cleaved by glucuronidase, such as the linker present in this formula:

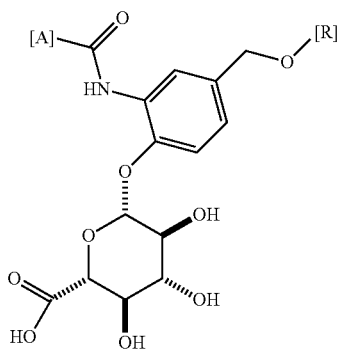

where [A] indicates a point of attachment to group A in Formula (I), and [R] represents a point of attachment to payload R. (*ACS Med. Chem. Letters*, vol. 1, 277-280 (2010). Such cleavable linkers would preferably be used as L$^3$ in Formula (I), but may also be used as L$^1$ and/or L$^2$.

The Payload (R) can be any moiety that is useful to attach to a protein. Many examples of compounds that can be usefully attached to proteins are known in the art. Examples include label moieties that enable a user to locate or identify the protein, including chelators that bind metal ions to provide detectability of the conjugate; binding moieties such as biotin or avidin, polynucleotides, antibodies or fragments thereof, poly-Arg or poly-lys containing 5-15 amino acid residues, etc., that make it easy to purify or isolate the protein or affix it to a surface; property-modifying groups such as fatty acid groups or polyethylene glycol (PEG); antigenic groups such as polysaccharides or cell surface proteins that are characteristic of a particular type of cell or bacterium; coupling groups that enable the modified protein or peptide to be attached to another molecule to make more complex conjugates, such as bispecific antibodies (see FIG. 2); and bioactive compounds including pharmaceutical compounds and radionuclides as well as cytotoxins, which can hitchhike on the protein to a desired tissue or cell where they can produce a desired effect. These hitchhiking compounds may act while they remain conjugated to the protein or a portion thereof, or they may first detach from the protein if the linking group is one that can readily cleave in vivo. Suitable pharmaceutical payloads for use with these methods include microtubule inhibitors, topoisomerase I inhibitors, intercalating agents, inhibitors of intracellular signaling pathways, kinase inhibitors, and DNA minor groove binders, including compound classes such as maytansinoids, auristatins, calicheamycins, psymberins, duocarmycins, anthracyclins, camptothecins, doxorubicins, taxols, pyrrolobenzodiazepines, and the like.

Specific examples of these pharmaceutical payloads having therapeutic or diagnostic uses include paclitaxel, docetaxel, etoposide, tenoposide, vincristine, vinblastine, colchicine, doxorubicin, daunorubicin, mithramycin, actinomycin, glucorticoids, puromycin, epirubicin, cyclophosphamide, methotrexate, cytarabine, f-fluorouracil, platins, streptozotocin, minomycin C, anthracyclines, dactinomycin or actinomycin, bleomycin, mithramycin, anthramycin, duocarmycins, ifosfamide, mitoxantrone, daunomycin, carminomycin, animoterin, melphalan, esperamicins, lexitropsins, auristatins (e.g., auristatin E, auristatin F, AEB, AEVB, AEFP, MMAE, MMAF), eleuthorobin, netropsin, podophyllotoxins, maytansiods including maytansine and DM1, and combretestatins.

Suitable coupling groups that can be used as payloads (groups that can be used to couple the conjugate to another moiety) include maleimide, thiols, alpha-halo ketones (e.g., —C(=O)—CH$_2$—X where X is chloro, bromo or iodo), carboxylic acids, amines, hydroxyls, alkenes, alkynes including cyclic octynes that can be used in copper-free 'click' chemistry, azide, and the like. Methods to use these coupling groups to connect the conjugates of the invention to other compounds having complementary coupling groups are well known in the art, and include Michael addition of a thiol to a maleimide, alkylation of a thiol with an alpha-haloketone, amide bond formation between amine and a carboxylic acid, 'click' chemistry (see, e.g., Meldal, et al., *Chem Rev.*, vol 108, 2952-3015 (2008)) to link an azide to an alkyne by forming a 1,2,3-triazole ring, and 'copper-free click' chemistry. See e.g., Meeuwissen, et al. *Polymer Chemistry*, vol. 3, 1783-95 (2012). 'Complementary' coupling groups are two coupling groups that readily combine to form a covalent bond, such as the pairs mentioned above

9

(carboxylate plus amine to form an amide; azide plus alkyne to form a 1,2,3-triazole; maleimide plus thiol, where the thiol adds to the double bond via a Michael addition; alpha-halo ketone plus thiol which form an alpha-thio ketone by alkylation of the thiol; etc.) In particular examples, a coupling group to serve as a Payload (R) is selected from the group consisting of halogen, —C≡CH, —C=CH$_2$, —OH, —SH, —SO$_2$—CH=CH$_2$, —O—NH$_2$, —N$_3$, —O—P(O)(OH)$_2$, —C(O)—H, —C(O)—CH$_3$, —NH—C(O)—CH$_2$—I, maleimidyl, 3,5-dioxo-1,2,4-triazolidin-4-yl, 1H-pyrrole-2,5-dione-1-yl, pyridin-2-yl-disulfanyl, tetrahydro-1H-thieno[3,4-d]imidazol-2(3H)-one-4-yl, 1-carbonyloxy-2,5-dioxopyrrolidine, sodium 1-carbonyloxy-2,5-dioxopyrrolidine-3-sulfonate, —SSR$^1$, —C(O)—OR$^1$, —N(R$^1$)H, —NH—N(R$^1$)H, where R$^1$ is H or (C$_1$-C$_6$)alkyl, and —C(O)—R$^2$, where R$^2$ is H, (C$_1$-C$_4$) alkyl, halo-substituted (C$_1$-C$_4$)alkyl, —CH=CH$_2$, N(R$^1$)H, or —NH—N(R$^1$)H.

The following enumerated embodiments illustrate particular aspects of the invention.

1. A polypeptide-payload conjugate comprising:

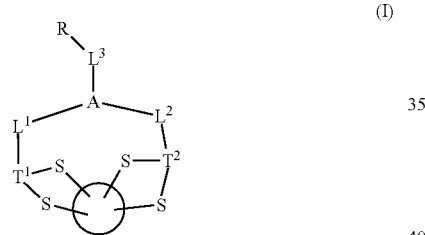

wherein the circle represents a polypeptide or polypeptide complex, which may comprise modifications other than the one shown;
each S is a sulfur atom of a cysteine residue of the polypeptide or polypeptide complex;
T$^1$ and T$^2$ each represent a tether that connects two sulfur atoms through 1-5 carbon atoms, wherein T$^1$ also attaches to L$^1$ and T$^2$ also attaches to L$^2$;
L$^1$ and L$^2$ each represent a linking group connecting T$^1$ or T$^2$, respectively, to A;
L$^3$ is a linking group that connects A to R;
A represents a group connecting L$^1$, L$^2$ and L$^3$;
and R represents a payload or a reactive functional group for attaching a payload.

2. The polypeptide-payload conjugate of embodiment 1, wherein the polypeptide is an antibody or an antibody Fc.

3. The polypeptide-payload conjugate of embodiment 1 or 2, wherein each of T$^1$ and T$^2$ comprises a chain of three carbon atoms connecting the attached sulfur atoms.

4. The polypeptide-payload conjugate of any of embodiments 1-3, wherein T$^1$ represents a group of the formula —CH$_2$—C(=N—O—[L$^1$])-CH$_2$—, wherein [L$^1$] indicates the point of attachment of T$^1$ to L$^1$.

5. The polypeptide-payload conjugate of any of embodiments 1-4, wherein T$^2$ represents a group of the formula

10

—CH$_2$—C(=N—O—[L$^2$])-CH$_2$—, wherein [L$^2$] indicates the point of attachment of T$^2$ to L$^2$.

6. The polypeptide-payload conjugate of any of embodiments 1-5, wherein L$^1$ and L$^2$ are the same.

7. The polypeptide-payload conjugate of any of embodiments 1-6, wherein the polypeptide is an antibody or antibody Fc, and the two sulfur atoms attached to T$^1$ formed a disulfide bind in the unconjugated antibody or antibody Fc.

8. The polypeptide-payload conjugate of any of embodiments 1-7, wherein the polypeptide is an antibody or antibody Fc, and the two sulfur atoms attached to T$^2$ formed a disulfide bind in the unconjugated polypeptide.

9. The polypeptide-payload conjugate of any of embodiments 1-8, wherein R represents a therapeutic agent, a detectable label, an antigen, or a binding group.

10. The polypeptide-payload conjugate of embodiment 9, wherein R represents a cytotoxin.

11. The polypeptide-payload conjugate of any of embodiments 1-10, wherein A is N, CH, phenyl, C$_{3-6}$ cycloalkyl, or a 5-6 membered heterocyclic or heteroaryl group having up to two heteroatoms selected from N, O and S as ring members.

12. The polypeptide-payload conjugate of any of embodiments 1-11, which is of the formula

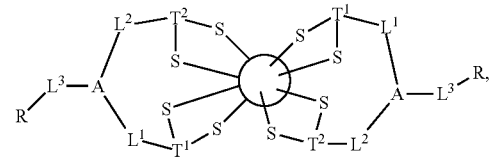

wherein the circle represents an antibody.

13. A compound of the formula (IIa)

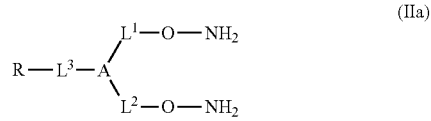

wherein R is a therapeutic agent, a detectable label, or a functional group selected from N$_3$, COOH, NH$_2$, SH, —S—Ar, maleimide, and HC≡C—, where Ar represents phenyl or pyridyl;
L$^1$, L$^2$ and L$^3$ are linking groups; and
A is N, CH, phenyl, C$_{3-6}$ cycloalkyl, or a 5-6 membered heterocyclic or heteroaryl group having up to two heteroatoms selected from N, O and S as ring members;
or a salt thereof.

14. The compound of embodiment 13, wherein L$^1$ and L$^2$ are the same.

15. The compound of embodiment 13 or 14, wherein R is a cytotoxin.

16. The compound of embodiment 13 or 14, wherein L$^3$ comprises at least one group selected from —(CH$_2$)$_{1-6}$—, —(CH$_2$CH$_2$O)$_{1-6}$— and —(OCH$_2$CH$_2$)$_{1-6}$—.

17. The compound of any one of embodiments 13-16, which is of the formula

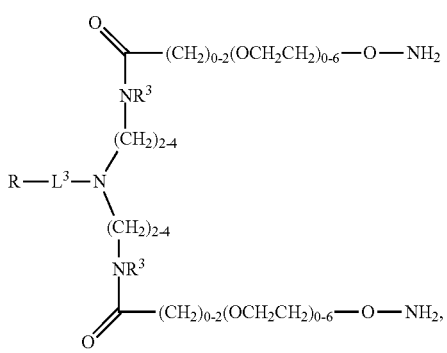

where $R^3$ is H or $(C_1-C_6)$alkyl.

18. The compound of any one of embodiments 13-17, wherein R-L³- is of the formula R—Z—C(=O)—, wherein Z comprises at least one group selected from —(CH₂)₁₋₆—, —(CH₂CH₂O)₁₋₆— and —(OCH₂CH₂)₁₋₆—.

19. A method to prepare a polypeptide-payload conjugate, which comprises contacting an activated polypeptide or polypeptide complex of formula (IIIa) or (IIIb):

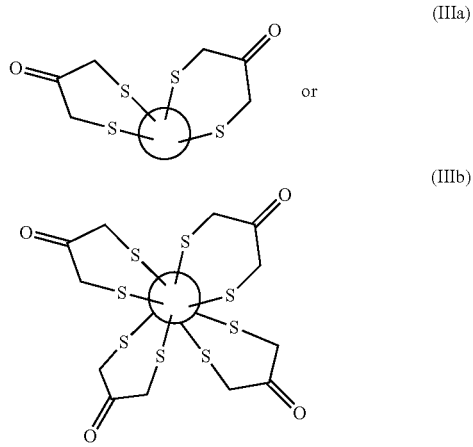

wherein the circle represents a polypeptide or polypeptide complex, which is activated by the inserted carbonyl groups, and each S represents a sulfur atom of a cysteine residue comprised in the polypeptide or polypeptide complex, with the compound of any one of embodiments 13-18.

20. The method of embodiment 19, wherein the polypeptide or polypeptide complex is an antibody or an Fc portion of an antibody.

21. The method of embodiment 19 or 20, which further comprises a step of preparing the activated polypeptide or polypeptide complex by a method that comprises reducing at least two disulfide bonds of an antibody or antibody Fc to make a reduced polypeptide or polypeptide complex, and contacting the reduced polypeptide or polypeptide complex with dichloroacetone to provide the activated polypeptide or polypeptide complex.

22. A pharmaceutical composition comprising the polypeptide-payload conjugate of any of embodiments 1-11 and at least one pharmaceutically acceptable carrier, diluent, or buffer.

The methods of the invention involve reducing a disulfide of a protein to be modified, forming a reduced protein that contains two free thiol groups. The reduced protein is contacted with a functionalized tethering compound that is capable of reacting with both of the free thiols on the reduced protein to tether the free thiols together, while also retaining at least one functional group on the tether that is suitable for conjugation; or alternatively the group to be attached may already be connected to the tethering group before the tethering group is added to the protein. In some embodiments, the functional group on the tether is a carbonyl group, e.g., the ketone obtained when the free thiols are allowed to react with a 1,3-dihaloketone (see FIG. 1). Because the free thiols are strongly nucleophilic, they react readily with electrophiles such as alkyl halides or alkyl tosylates, via irreversible reactions that involve displacing a leaving group and forming a covalent sulfur-carbon bond. Some suitable examples of functionalized carbonyl-containing tethering compounds include 1,3-dichloroacetone and 1,3-dibromoacetone. These reagents have been used to provide stabilization of disulfide moieties in small cyclic peptides by tethering sulfhydryls together. See e.g. WO2008/157380 (reaction of dichloroacetone with a reduced cyclic pentapeptide, followed by reduction of the carbonyl). Sulfonates of 1,3-dihydroxyacetone (e.g., mesylate, triflate, phenylsulfonate, tosylate, and the like) can also be used. These reagents are sufficiently reactive toward the free thiols of a reduced protein to provide reasonably rapid reaction to form an activated protein with two cysteine residues tethered together, wherein each of the free thiols is covalently attached to the functionalized tethering group.

Figure 1:
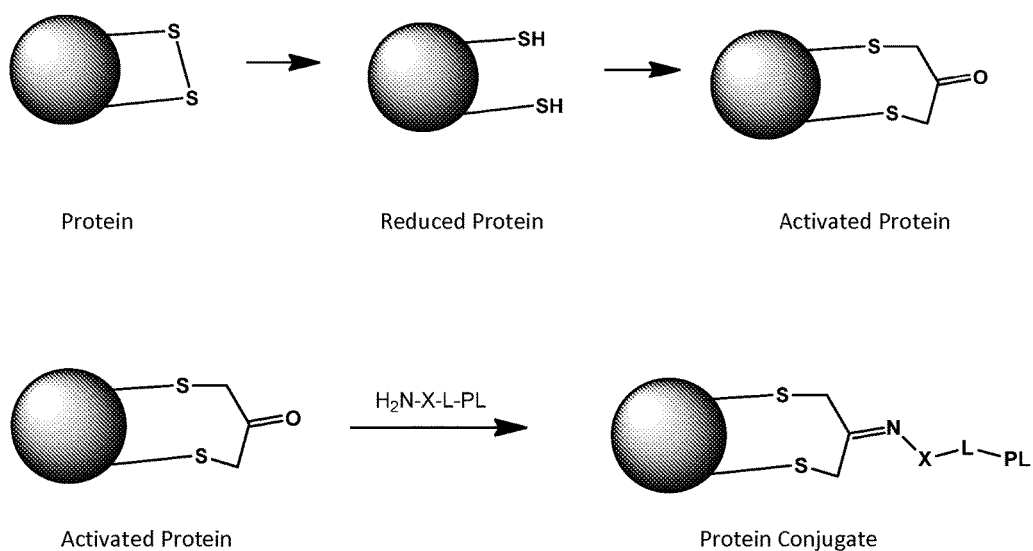
FIG. 1 is a scheme illustrating how a disulfide can be activated and used to make a polypeptide-payload conjugate.

The reduced protein and functionalized tethering compound are contacted under conditions suitable to promote reaction between the tethering compound and the two free thiols of the reduced protein, and particularly under conditions of concentration and temperature that favor causing both of the free thiols that were previously joined in a disulfide bond to react with a single molecule of the tethering compound so they are once again tied together, but now with a short tether connecting them instead of a direct disulfide bond. This reaction forms an activated protein as illustrated in FIG. 1, having a functionalized tether [—CH₂C(O)—CH₂—] between the two sulfur atoms. The tether in FIG. 1 includes a carbonyl that can be used to efficiently attach a payload via clean and efficient Schiff base formation chemistry.

For the present invention, at least two disulfides are reduced and used for conjugation. When the tethering group contains a reactive ketone to serve as the conjugation site, as depicted in FIG. 1, the protein will typically be activated with two tethering groups, which will ordinarily be the same. The two activated tethering groups will then be linked together by reaction with a bridging reagent having two aminooxy groups—see FIG. 3. The bridging group then provides an attachment point for a payload.

It is understood throughout this discussion that the protein, even though it is depicted as a circle or sphere, can be a small polypeptide of fewer than 10 amino acids or a large enzyme or a complex of two or more subunits or polypeptide strands. The two sulfur atoms of the disulfide can be on one subunit of a multimeric complex, or they can be on different strands of a protein complex. In addition to the disulfide participating in the transformations described herein, the protein may also contain other disulfide linkages that may be reduced, or may not be reduced due to their location within the protein. The methods of the invention can utilize known methods to selectively reduce solvent-accessible disulfide linkages near the surface of the folded protein, often without reducing 'buried' disulfides that may be essential for maintaining the overall shape and functionality of the protein, or for keeping two subunits linked together in a multi-subunit complex.

Once the activated protein has been formed, a payload can be attached by suitable methods, such as oxime formation when the tether contains a reactive ketone. As illustrated in FIGS. 3A-3C and certain of the examples, a bis-aminooxy compound containing the payload can be added in one step; alternatively, an alkoxyamine having a functional group can be added to the tether, and the functional group can be used to attach the payload in a subsequent step.

The activated protein is typically contacted with an aminooxy compound containing a payload, or a group that can be used to attach a payload, without purifying or isolating the activated protein. The Examples illustrate introducing a reactive group onto the protein first, then using the reactive group to attach a cytotoxin.

EXAMPLES

The following HPLC methods are used in the examples below.

Method A;
Eluent A: water+0.1% Formic acid, Eluent B: Acetonitrile+0.08% Formic acid
Gradient: from 3 to 80% B in 2 min–Flow 1.0 ml/min.
Column: Proswift Monolith 4.6*50 mm 40° C.

Method B;
Eluent A: water+0.1% Formic acid, Eluent B: Acetonitrile+0.04% Formic acid
Gradient: from 3 to 80% B in 2 min–Flow 1.0 ml/min.
Column: Proswift Monolith 4.6*50 mm 40° C.

Method C;
Eluent A: water+3.75 mM ammonium acetate+2% acetonitrile, Eluent B: Acetonitrile
Gradient: from 2 to 98% B in 1.7 min–Flow 1.0 ml/min.
Column: Acquity CSH 2.1*50 mm 50° C.

Method D (HRMS);
Eluent A: water+0.05% Formic acid+3.75 mM ammonium acetate, Eluent B: Acetonitrile+0.04% Formic acid.
Gradient: from 2 to 98% B in 4.4 min–Flow 1.0 ml/min.
Column: Acquity CSH 2.1*50 mm 50° C.

Preparation of Aminooxy Compounds (1)

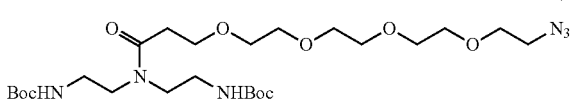

NHS-PEG$_4$-azide (50 mg, 0.129 mmol) and triethylamine (72 µL, 0.515 mmol) were added to 1,7-bis-Boc-1,4,7-triazaheptane (47 mg, 0.155 mmol) in dichloromethane (1.3 mL). The resulting mixture was stirred at room temperature for 1 hour. Saturated aqueous sodium chloride was added, and the mixture was extracted with dichloromethane twice, and the combined extracts were dried over anhydrous magnesium sulfate. After filtration and concentration, the residue was purified by silica gel chromatography (0-40%, v/v, ethyl acetate/heptane) to the title compound 1 (30 mg, 40%). LC-MS (M+1) 577.4, t=1.20 minutes. HRMS: calculated for $C_{25}H_{49}N_6O_9$ (MH+) 577.3561, observed 577.3548. $^1$H NMR (400 MHz, CDCl$_3$) δ ppm 1.44 (br. s., 18H) 2.63 (t, J=6.28 Hz, 2H) 3.27-3.34 (m, 4H) 3.40 (t, J=5.04 Hz, 2H) 3.46-3.51 (m, 4H) 3.54-3.72 (m, 14H) 3.80 (t, J=6.33 Hz, 2H) 5.11 (br. s., 1H) 5.18 (br. s., 1H).

N,N-bis(2-aminoethyl)-1-azido-3,6,9,12-tetraoxapentadecan-15-amide dihydrochloride (2)

(2)

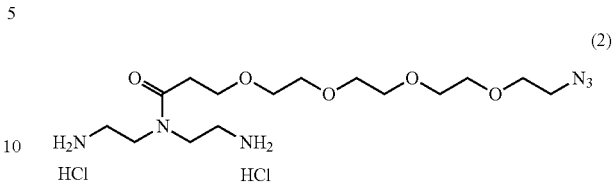

HCl 4N in dioxane (130 µL, 0.52 mmol) was added dropwise to a solution of 1 (30 mg, 0.052 mmol) in dichloromethane (1 mL). The resulting mixture was stirred at room temperature for 30 minutes, and then concentrated in vacuo and the title compound N,N-bis(2-aminoethyl)-1-azido-3,6,9,12-tetraoxapentadecan-15-amide dihydrochloride (2, 14 mg, 60%) was obtained. LC-MS (M+1) 377.3, t=0.44 minutes 1-azido-N,N-bis(1-((1,3-dioxoisoindolin-2-yl)oxy)-15-oxo-3,6,9,12-tetraoxa-16-azaoctadecan-18-yl)-3,6,9,12-tetraoxapentadecan-15-amide (3)

(3)

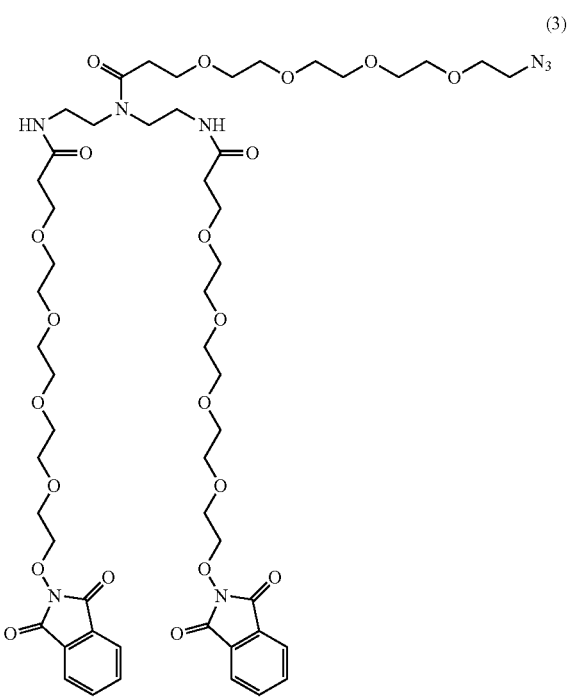 [SMILES: [N-]=[N+]=NCCOCCOCCOCCOCCC(=O)N(CCNC(=O)CCOCCOCCOCCOCCON1C(=O)c2ccccc2C1=O)CCNC(=O)CCOCCOCCOCCOCCON1C(=O)c2ccccc2C1=O]

2,5-dioxopyrrolidin-1-yl 1-((1,3-dioxoisoindolin-2-yl)oxy)-3,6,9,12-tetraoxapentadecan-15-oate (35 mg, 0.069 mmol) and triethylamine (17 µL, 0.125 mmol) were added to a solution of N,N-bis(2-aminoethyl)-1-azido-3,6,9,12-tetraoxapentadecan-15-amide dihydrochloride (2, 14 mg, 0.031 mmol) in dichloromethane. The resulting mixture was stirred at room temperature for 16 hours, and then concentrated in vacuo. The title compound 1-azido-N,N-bis(1-((1,3-dioxoisoindolin-2-yl)oxy)-15-oxo-3,6,9,12-tetraoxa-16-azaoctadecan-18-yl)-3,6,9,12-tetraoxapentadecan-15-amide (3, 0.031 mmol) was obtained. LC-MS (M+1) 1163.6, t=1.12 minutes.

N,N-bis(1-(aminooxy)-15-oxo-3,6,9,12-tetraoxa-16-azaoctadecan-18-yl)-1-azido-3,6,9,12-tetraoxapentadecan-15-amide (4)

(4)

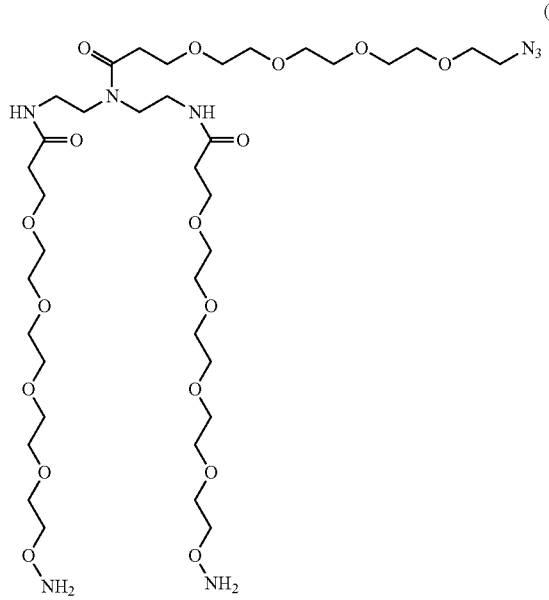

Hydrazine monohydrate (61 μL, 1.24 mmol) was added to a solution of 1-azido-N,N-bis(1-((1,3-dioxoisoindolin-2-yl)oxy)-15-oxo-3,6,9,12-tetraoxa-16-azaoctadecan-18-yl)-3,6,9,12-tetraoxapentadecan-15-amide (3, 0.031 mmol) in dichloromethane (0.6 mL). The resulting mixture was stirred at room temperature for 1 hour, and then concentrated in vacuo. The resulting residue was purified by preparative HPLC (15-40%, v/v, acetonitrile/(5 mM aqueous NH$_4$OH)) and the combined elutes were concentrated to yield the title compound N,N-bis(1-(aminooxy)-15-oxo-3,6,9,12-tetraoxa-16-azaoctadecan-18-yl)-1-azido-3,6,9,12-tetraoxapentadecan-15-amide (4, 13 mg, 46%). LC-MS (M+1) 903.6, t=0.65 minutes. $^1$H NMR (400 MHz, CDCl$_3$) δ ppm 2.41-2.53 (m, 4H) 2.66 (t, J=6.42 Hz, 2H) 3.37-3.45 (m, 6H) 3.45-3.54 (m, 4H) 3.56-3.71 (m, 44H) 3.71-3.76 (m, 4H) 3.78 (t, J=6.37 Hz, 2H) 3.86 (br. s., 4H).

di-tert-butyl(((6-(3-(pyridin-2-yldisulfanyl)propanamido)hexanoyl)azanediyl)bis(ethane-2,1-diyl))dicarbamate (5)

(5)

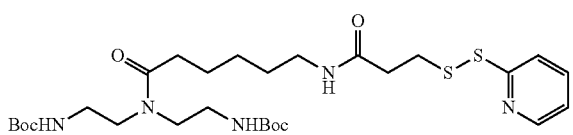

Succinimidyl 6-(3-[2-pyridyldithio]-propionamido)hexanoate (50 mg, 0.118 mmol) and triethylamine (65 μL, 0.47 mmol) were added to a solution of 1,7-bis-Boc-1,4,7-triazaheptane (43 mg, 0.141 mmol) in dichloromethane (1.2 mL). The resulting mixture was stirred at room temperature for 1 hour. N,N-diisopropylethylamine (82 μL, 0.47 mmol) was added, and the mixture was stirred at room temperature for 16 hours. Saturated aqueous sodium chloride was added, and then the mixture was extracted twice with dichloromethane. The combined extracts were dried over anhydrous magnesium sulfate. After filtration and concentration, the residue was purified by silica gel chromatography (0-5%, v/v, methanol/dichloromethane) to give di-tert-butyl ((((6-(3-(pyridin-2-yldisulfanyl)propanamido)hexanoyl)azanediyl)bis(ethane-2,1-diyl))dicarbamate (5, 42 mg, 58%) as colorless solid. LC-MS (M+1) 614.3, t=1.21 minutes. HRMS: calculated for C$_{28}$H$_{48}$N$_5$O$_6$S$_2$ (MH+) 614.3046, observed 614.3065. $^1$H NMR (400 MHz, CDCl$_3$) δ ppm 1.31-1.74 (m, 24H) 2.37 (t, J=7.03 Hz, 2H) 2.64 (t, J=6.72 Hz, 2H) 3.11 (t, J=6.72 Hz, 2H) 3.20-3.38 (m, 6H) 3.44-3.50 (m, 4H) 5.20-5.34 (m, 2H) 6.78 (br. s., 1H) 7.19 (br. s., 1H) 7.74 (br. s., 2H) 8.50 (d, J=3.42 Hz, 1H).

Preparation of intermediate N,N-bis(2-aminoethyl)-6-(3-(pyridin-2-yldisulfanyl)propanamido)hexanamide dihydrochloride (6)

(6)

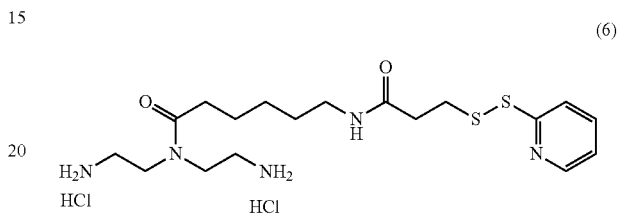

HCl 4N in dioxane (171 μL, 0.68 mmol) was added to a solution of di-tert-butyl ((((6-(3-(pyridin-2-yldisulfanyl)propanamido)hexanoyl)azanediyl)bis(ethane-2,1-diyl))dicarbamate (5, 42 mg, 0.068 mmol) in dichloromethane (0.7 mL). The resulting mixture was stirred at room temperature for 30 minutes, and then concentrated in vacuo to yield the title compound N,N-bis(2-aminoethyl)-6-(3-(pyridin-2-yldisulfanyl)propanamido)hexanamide dihydrochloride (6, 0.068 mmol). LC-MS (M+1) 414.2, t=0.52 minutes.

1-((1,3-dioxoisoindolin-2-yl)oxy)-N-(14(1,3-dioxoisoindolin-2-yl)oxy)-15-oxo-19-(6-(3-(pyridin-2-yldisulfanyl)propanamido)hexanoyl-3,6,9,12-tetraoxa-16,19-diazahenicosan-21-yl)-3,6,9,12-tetraoxapentadecan-15-amide (7)

(7)

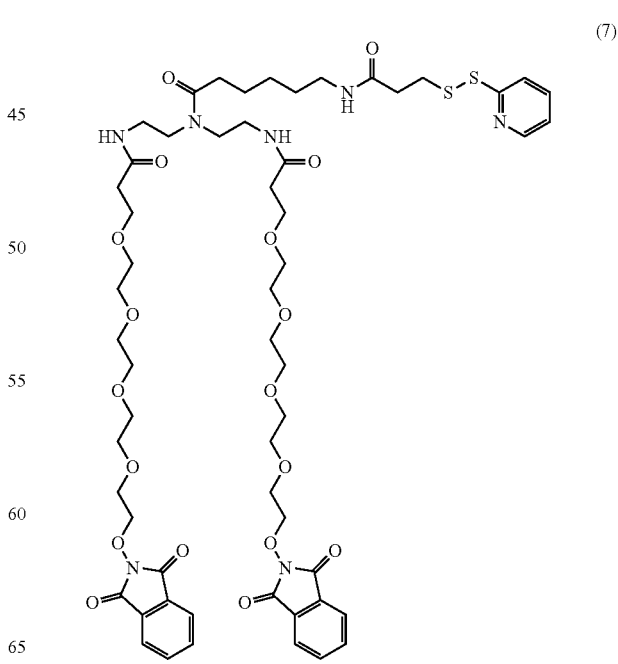

2,5-dioxopyrrolidin-1-yl 1-((1,3-dioxoisoindolin-2-yl)oxy)-3,6,9,12-tetraoxapentadecan-15-oate (76 mg, 0.150 mmol) and triethylamine (38 μL, 0.272 mmol) were added to a solution of N,N-bis(2-aminoethyl)-6-(3-(pyridin-2-yldisulfanyl)propanamido)hexanamide dihydrochloride (6, 0.068 mmol) in dichloromethane (1.4 mL). The resulting mixture was stirred at room temperature for 16 hours. Saturated aqueous sodium chloride was added, and the mixture was extracted twice with dichloromethane. The combined extracts were dried over anhydrous magnesium sulfate. After filtration and concentration, the residue was purified by silica gel chromatography (0-10%, v/v, methanol/dichloromethane) to give 1-((1,3-dioxoisoindolin-2-yl)oxy)-N-(1-((1,3-dioxoisoindolin-2-yl)oxy)-15-oxo-19-(6-(3-(pyridin-2-yldisulfanyl)propanamido)hexanoyl)-3,6,9,12-tetraoxa-16,19-diazahenicosan-21-yl)-3,6,9,12-tetraoxapentadecan-15-amide (7, 47 mg, 58%) as clear oil. LC-MS (M+1) 1200.4, t=1.13 minutes. HRMS: calculated for C$_{56}$H$_{78}$N$_{7}$O$_{18}$S$_{2}$ (MH+) 1200.4845, observed 1200.4943. $^{1}$H NMR (400 MHz, CDCl$_{3}$) δ ppm 1.31-1.74 (m, 6H) 2.40 (t, J=7.21 Hz, 2H) 2.43-2.57 (m, 4H) 2.66 (t, J=6.72 Hz, 2H) 3.12 (t, J=6.97 Hz, 2H) 3.29 (q, J=6.44 Hz, 2H) 3.35-3.55 (m, 9H) 3.55-3.67 (m, 19H) 3.67-3.80 (m, 8H) 3.88 (td, J=4.43, 2.26 Hz, 4H) 4.33-4.44 (m, 4H) 6.96 (br. s., 1H) 6.99-7.10 (m, 1H) 7.24 (br. s., 2H) 7.73-7.83 (m, 6H) 7.83-7.91 (m, 4H) 8.51 (d, J=4.77 Hz, 1H).

di-tert-butyl (((6-(3-(phenyldisulfanyl)propanamido)hexanoyl)azanediyl)bis(ethane-2,1-diyl))dicarbamate (8)

(8)

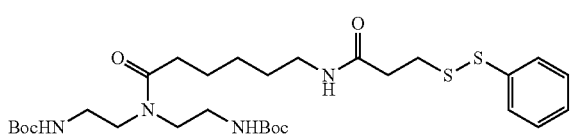

Thiophenol (101 μL, 0.98 mmol) was added to a solution of di-tert-butyl (((6-(3-(pyridin-2-yldisulfanyl)propanamido)hexanoyl)azanediyl)bis(ethane-2,1-diyl))dicarbamate (5, 60 mg, 0.098 mmol) in dichloromethane (0.98 mL). The resulting mixture was stirred at room temperature for 30 minutes, and the mixture was concentrated in vacuo. The residue was purified by silica gel chromatography ((10-100%, v/v, ethyl acetate/heptane) to give di-tert-butyl (((6-(3-(phenyldisulfanyl)propanamido)hexanoyl)azanediyl)bis(ethane-2,1-diyl))dicarbamate (8, 35 mg, 58%) as clear oil. LC-MS (M+1) 613.2, t=1.38 minutes. HRMS: calculated for C$_{29}$H$_{49}$N$_{4}$O$_{6}$S$_{2}$ (MH+) 613.3094, observed 613.3097. $^{1}$H NMR (400 MHz, CDCl$_{3}$) δ ppm 1.29-1.55 (m, 22H) 1.55-1.78 (m, 2H) 2.35 (t, J=7.20 Hz, 2H) 2.56 (t, J=7.01 Hz, 2H) 3.03 (t, J=7.01 Hz, 2H) 3.16-3.36 (m, 6H) 3.37-3.53 (m, 4H) 7.14-7.30 (m, 1H) 7.30-7.41 (m, 2H) 7.47-7.59 (m, 2H).

Preparation of intermediate N,N-bis(2-aminoethyl)-6-(3-(phenyldisulfanyl)propanamido)hexanamide dihydrochloride (9)

(9)

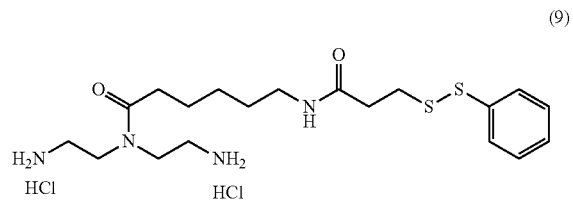 [SMILES: NCCN(CCN)C(=O)CCCCCNC(=O)CCSSc1ccccc1 ; Cl ; Cl]

HCl 4N in dioxane (143 μL, 0.57 mmol) was added to a solution of di-tert-butyl (((6-(3-(phenyldisulfanyl)propanamido)hexanoyl)azanediyl)bis(ethane-2,1-diyl))dicarbamate (8, 35 mg, 0.057 mmol) in dichloromethane (0.6 mL). The resulting mixture was stirred at room temperature for 30 minutes, and the mixture was concentrated in vacuo to give N,N-bis(2-aminoethyl)-6-(3-(phenyldisulfanyl)propanamido)hexanamide dihydrochloride (9, 0.057 mmol). LC-MS (M+1) 413.2, t=0.67 minutes.

4-((1,3-dioxoisoindolin-2-yl)oxy)-N-(14(1,3-dioxoisoindolin-2-yl)oxy)-15-oxo-19-(6-(3-(phenyldisulfanyl)propanamido)hexanoyl)-3,6,9,12-tetraoxa-16,19-diazahenicosan-21-yl)-3,6,9,12-tetraoxapentadecan-15-amide (10)

(10)

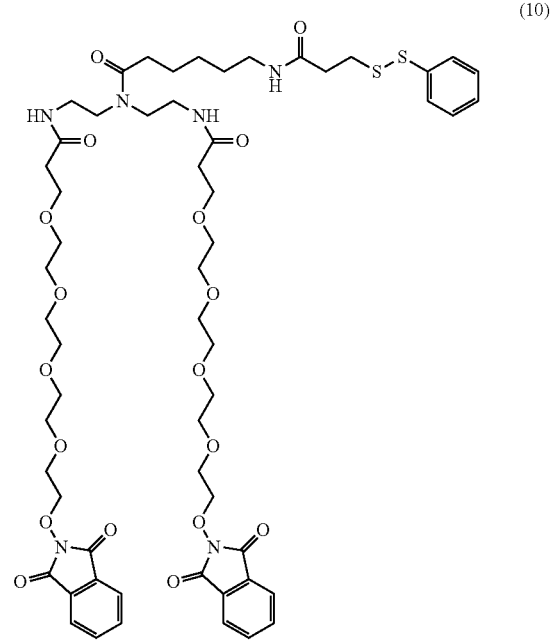 [SMILES: O=C(CCOCCOCCOCCOCCON1C(=O)c2ccccc2C1=O)NCCN(CCNC(=O)CCOCCOCCOCCOCCON1C(=O)c2ccccc2C1=O)C(=O)CCCCCNC(=O)CCSSc1ccccc1]

2,5-dioxopyrrolidin-1-yl 1-((1,3-dioxoisoindolin-2-yl)oxy)-3,6,9,12-tetraoxapentadecan-15-oate (87 mg, 0.171 mmol) and triethylamine (39 μL, 0.285 mmol) were added to a solution of N,N-bis(2-aminoethyl)-6-(3-(phenyldisulfanyl)propanamido)hexanamide dihydrochloride (9, 0.057 mmol) in dichloromethane (0.6 mL). The resulting mixture was stirred at room temperature for 1 hour. Saturated aqueous sodium chloride was added, and the mixture was extracted twice with dichloromethane. The combined extracts were dried over anhydrous magnesium sulfate. After filtration and concentration the residue was purified by silica gel chromatography (0-10%, v/v, methanol/dichloromethane) to give 1-((1,3-dioxoisoindolin-2-yl)oxy)-N-(1-((1,3-dioxoisoindolin-2-yl)oxy)-15-oxo-19-(6-(3-(phenyldisulfanyl)propanamido)hexanoyl)-3,6,9,12-tetraoxa-16,19-diazahenicosan-21-yl)-3,6,9,12-tetraoxapentadecan-15-amide (10, 45 mg, 66%) as clear oil. LC-MS (M+1) 1199.3, t=1.25 minutes. HRMS: calculated for $C_{57}H_{79}N_6O_{18}S_2$ (MH+) 1199.4892, observed 1199.4955. $^1$H NMR (400 MHz, CDCl$_3$) 6 ppm 1.32-1.44 (m, 2H) 1.44-1.60 (m, 4H) 2.41 (t, J=7.40 Hz, 2H) 2.49 (d, J=4.89 Hz, 4H) 2.60 (br. s., 2H) 3.04 (t, J=7.09 Hz, 2H) 3.25 (d, J=4.40 Hz, 2H) 3.44 (d, J=6.85 Hz, 6H) 3.52 (br. s., 3H) 3.56-3.78 (m, 27H) 3.88 (td, J=4.31, 2.75 Hz, 4H) 4.30-4.45 (m, 4H) 7.18-7.38 (m, 3H) 7.55 (dd, J=6.91, 1.65 Hz, 2H) 7.71-7.82 (m, 4H) 7.82-7.91 (m, 4H)

Preparation of intermediate 1-(aminooxy)-N-(1-(aminooxy)-15-oxo-19-(6-(3-(phenyldisulfanyl)propanamido)hexanoyl)-3,6,9,12-tetraoxa-16,19-diazahenicosan-21-yl)-3,6,9,12-tetraoxapentadecan-15-amide (11)

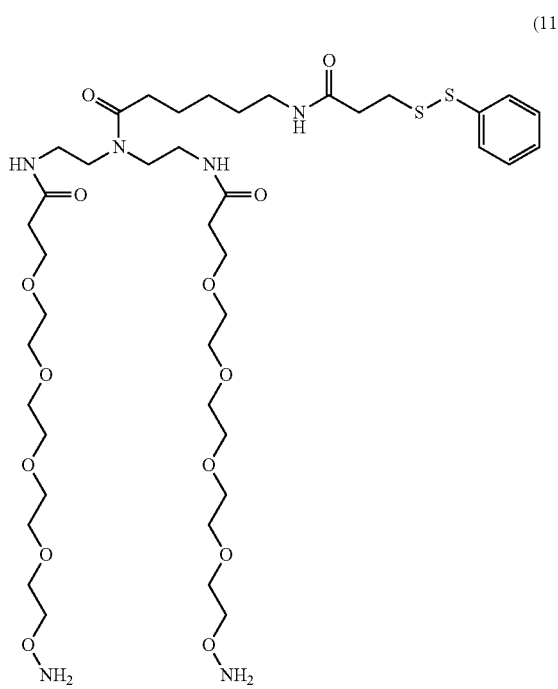 [SMILES: NOCCOCCOCCOCCOCCC(=O)NCCN(CCNC(=O)CCOCCOCCOCCOCCON)C(=O)CCCCCNC(=O)CCSSc1ccccc1]

(11)

Hydrazine monohydrate (74 μL, 1.501 mmol) was added to a solution of 1-((1,3-dioxoisoindolin-2-yl)oxy)-N-(1-((1,3-dioxoisoindolin-2-yl)oxy)-15-oxo-19-(6-(3-(phenyldisulfanyl)propanamido)hexanoyl)-3,6,9,12-tetraoxa-16,19-diazahenicosan-21-yl)-3,6,9,12-tetraoxapentadecan-15-amide (10, 45 mg, 0.038 mmol) in dichloromethane (0.75 mL). The resulting mixture was stirred at room temperature for 30 minutes, and then concentrated in vacuo. The residue was purified by preparative HPLC (15-40%, v/v, acetonitrile/(5 mM aqueous NH$_4$OH)). After concentration, 1-(aminooxy)-N-(1-(aminooxy)-15-oxo-19-(6-(3-(phenyldisulfanyl)propanamido)hexanoyl)-3,6,9,12-tetraoxa-16,19-diazahenicosan-21-yl)-3,6,9,12-tetraoxapentadecan-15-amide (11, 12 mg, 34%) was obtained. LC-MS ((M/2)+1) 470.6, t=1.15 minutes.

Preparation of Conjugates with Bioorthogonal Functional Group(s)

Preparation of Fc from IgG:

0.61 mL of Tris 0.1 M pH 8.0, and Lys-C (100 μL of a 0.1 mg/mL solution in water) were added sequentially to IgG (0.639 mL of a 78.26 mg/mL solution in PBS pH 7.4, 0.336 μmol). The resulting mixture was incubated at 37° C. for 45 minutes. Protein A immobilized on sepharose beads were added to the mixture, and subsequently washed three times with PBS buffer to remove Lys-C and Fab fragments. Then the Fc was released by adding glycine 0.1M pH 2.5 twice, eluting into Tris 1M pH 8.0. The eluted Fc was buffer exchanged to PBS pH 7.4 using Amicon 10K MWCO centrifugal filters to give Fc (700 μL, 19.6 mg/mL, 13.7 mg, 77%). LCMS ESI (after deglycosylation with PNGase F): 50410.

Preparation of 12

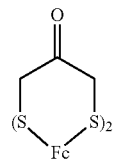

12

900 μL of Tris 0.25M pH 7.4, and 1,3-dichloroacetone in DMSO (120 μL, 0.019 mmol) were added sequentially to a solution of Fc (10 mg, 0.189 μmol) in 510 μL PBS pH 7.4 at 4° C. The mixture was agitated at 4° C. for 10 minutes, and then TCEP.HCl in water (180 μL, 1.887 μmol) was added dropwise. The mixture was agitated at 4° C. for 20 hours. The mixture was passed through Zeba 7K MWCO (Molecular Weight Cut Off) spin columns three times to give 12 (1.8 mL, 5.35 mg/mL, 9.63 mg, 96%). LCMS ESI (after deglycosylation with PNGase F): 50521.

Preparation of Modified Anti-Her2 IgG (13)

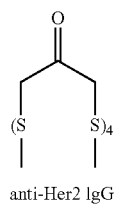

13

1,3-dichloroacetone in DMSO (9.72 μL, 1.53 μmol) was added to a solution of anti-Her2 IgG (1.5 mg, 0.010 μmol) in 82 μL of Tris (0.25M pH 7.4) at 4° C. The mixture was agitated at 4° C. for 10 minutes, and then TCEP.HCl in water (14.62 μL, 0.153 μmol) was added dropwise. The resulting mixture was agitated at 4° C. for 20 hours and then passed through Zeba 7K MWCO spin columns three consecutive times to give modified anti-Her2 IgG 13 (110 μL, 11.6 mg/mL, 1.27 mg, 85%). LCMS ESI (after deglycosylation with PNGase F): 145401.

Example 1. Preparation of Fc-Azido Conjugate (14)

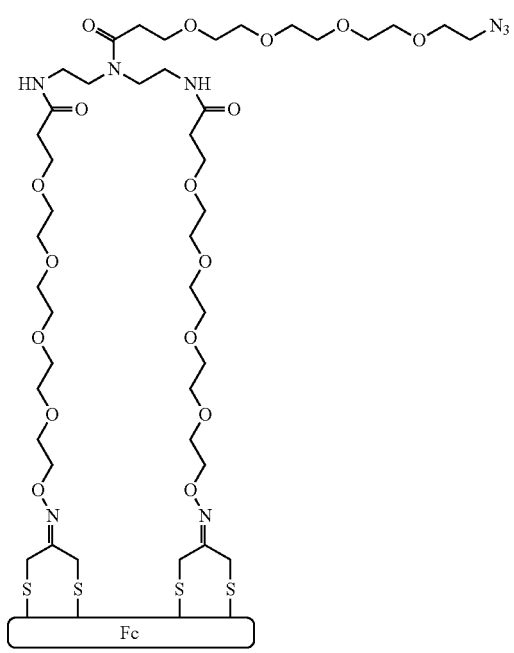

Figure 4:
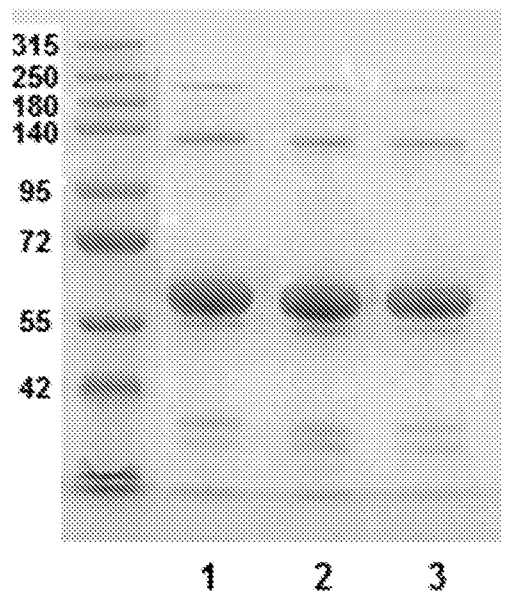
FIG. 4 shows the SDS-PAGE gel of the Fc, 12, and 14 (Example 1).

0.4 mL of PBS pH 7.4, N,N-bis(1-(aminooxy)-15-oxo-3,6,9,12-tetraoxa-16-azaoctadecan-18-yl)-1-azido-3,6,9,12-tetraoxapentadecan-15-amide (4, 52 µL of a 30 mg/mL solution in DMSO, 1.55 mg, 1.717 µmol), and 3,5-diaminobenzoic acid in DMSO (130 µL, 0.172 mmol) were added sequentially to a solution of 12 (9.1 mg, 0.172 µmol) in 1.7 mL of PBS (pH 7.4) at room temperature. The mixture was agitated at 20° C. for 16 hours, and then concentrated by using Amicon ultra 10K MWCO centrifugal filter with PBS as the washing buffer to give the title compound 14 (310 µL, 27 mg/mL, 8.37 mg, 90%). LCMS ESI (after deglycosylation with PNGase F): 51388. See FIG. 4 for the SDS-PAGE of the reaction product along with Fc and 12.

Example 2. Preparation of Anti-Her2 IgG with Diazido Functions (15)

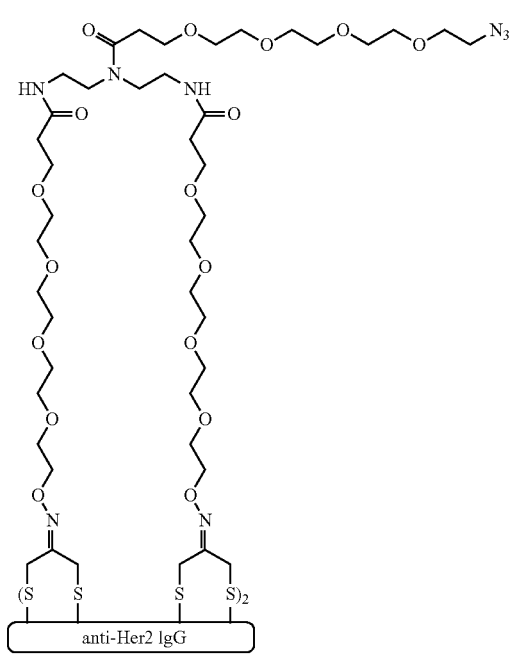

Figure 5:
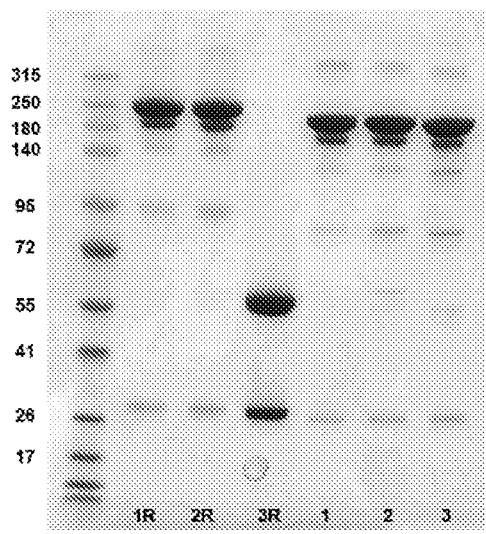
FIG. 5 shows the SDS-PAGE gel of the products of Example 2.

N,N-bis(1-(aminooxy)-15-oxo-3,6,9,12-tetraoxa-16-azaoctadecan-18-yl)-1-azido-3,6,9,12-tetraoxapentadecan-15-amide (4, 1.81 µL of a 30 mg/mL solution in DMSO, 54 µg, 0.060 µmol), and 3,5-diaminobenzoic acid in DMSO (2.28 µL, 3.00 µmol) were added sequentially to the modified anti-Her2 IgG (13, 441 µg, 0.003 µmol) in 38 µL of PBS (pH 7.4) at room temperature. The resulting mixture was agitated at 20° C. for 16 hours, and then passed through Zeba 7K MWCO spin columns three consecutive times to give the title compound (15, 125 µL, 3.05 mg/mL, 380 µg, 85%). LCMS ESI (after deglycosylation with PNGase F): 147132. See FIG. 5 for SDS-PAGE of this product along with the antibody alone (TBS) and another TBS conjugate not included here.

Example 3. Preparation of Anti-Her2 IgG with-Phenyldisulfides 16

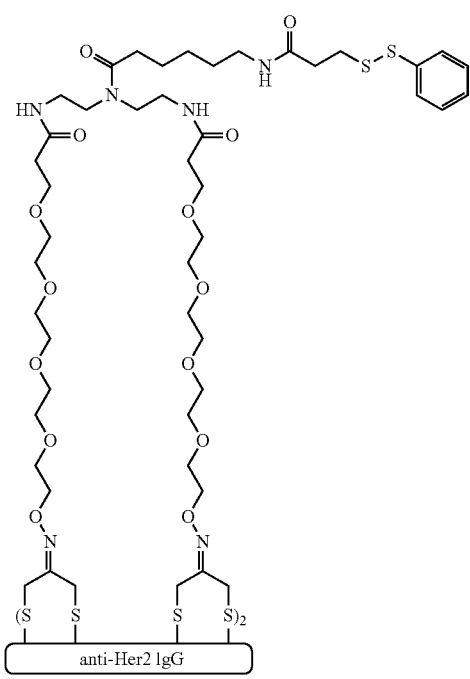

1-(aminooxy)-N-(1-(aminooxy)-15-oxo-19-(6-(3-(phenyldisulfanyl)propanamido)hexanoyl)-3,6,9,12-tetraoxa-16,19-diazahenicosan-21-yl)-3,6,9,12-tetraoxapentadecan-15-amide (11, 8.44 µL of a 30 mg/mL solution in DMSO, 253 µg, 0.269 µmol), and 3,5-diaminobenzoic acid in DMSO (5.12 µL, 6.74 µmol) were added to the modified anti-Her2 IgG (13, 2 mg, 0.013 µmol) in 135 µL of PBS (pH 7.4) at room temperature. The mixture was agitated at 20° C. for 16 hours, and then passed through Zeba 7K MWCO spin columns three consecutive times to give the title compound 16 (150 µL, 9.24 mg/mL, 1.4 mg, 69%). LCMS ESI (after deglycosylation with PNGase F): 147204.

Preparation of Conjugates with Cytotoxin Payloads

Example 5. Preparation of Anti-Her2 IgG-diMMAF 17

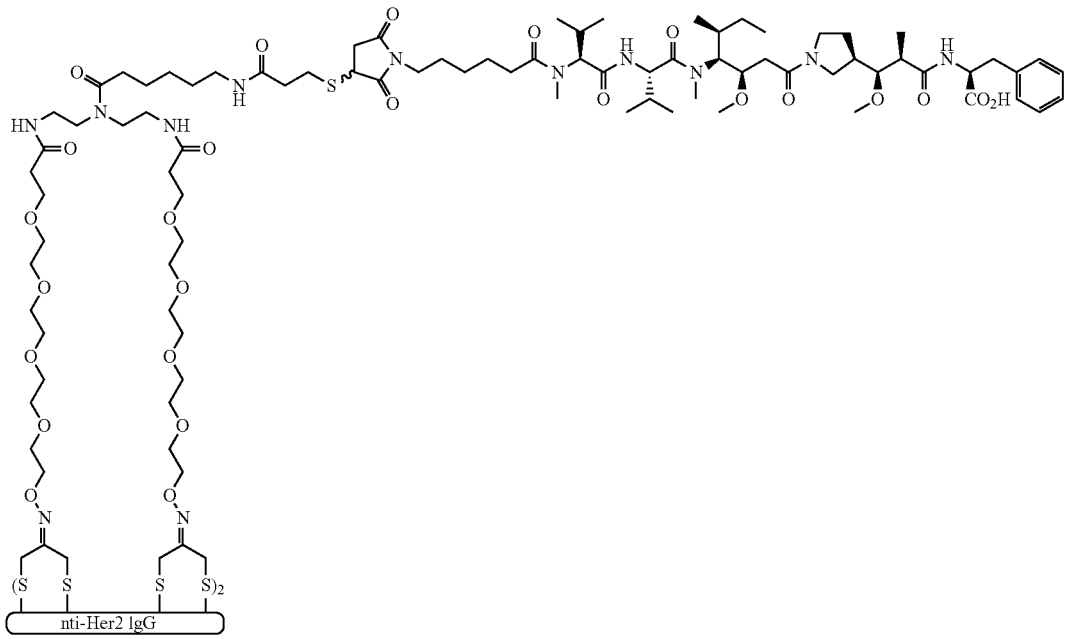

Figure 6:
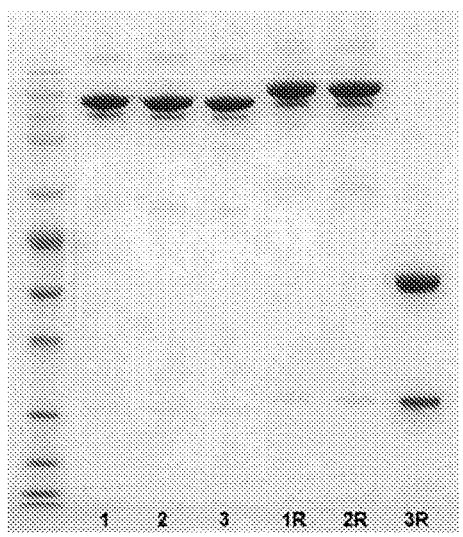
FIG. 6 shows the SDS-PAGE gel of the products of Examples 4 and 5.

A solution of TCEP.HCl in water (0.88 μL, 0.092 μmol) was added dropwise to anti-Her2 IgG with-phenyldisulfides 16 (0.69 mg, 0.0046 μmol) in 75 μL of PBS (pH 7.4) at room temperature. The resulting mixture was agitated at 20° C. for 20 minutes, and then passed through Zeba 7K MWCO spin columns (pre-equilibrated with PBS 0.1M+EDTA 10 mM, pH 7.4) three consecutive times. (S)-2-((2R,3S)-3-((R)-1-((3R,4S,5S)-4-((R)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)pyrrolidin-3-yl)-3-methoxy-2-methylpropanamido)-3-phenylpropanoic acid (4.27 μL, 0.092 μmol, 20 mg/mL in DMSO) was then added, and the mixture was agitated at 20° C. for 16 hours. The mixture was passed through Zeba 7K MWCO spin columns three consecutive times to give the title compound 17 (100 μL, 4.93 mg/mL, 493 μg, 70%). LCMS ESI (after deglycosylation with PNGase F): 146987 (10% by peak intensity, anti-Her2 IgG-linker, +0 MMAF), 148839 (90% by peak intensity, anti-Her2 IgG-diMMAF, +2 MMAF). The average DAR for the final product was estimated as 1.8 based on ESI-MS peaks. See FIG. 6 for the SDS-PAGE of this product along with the precursor and anti-Her2 IgG.

Preparation of Reduced Samples for SDS PAGE (Reducing Gel Protocol):

Into PBS solution of proteins (5 μg, 0.00017 μmol) was added TCEP HCl solution (1 μl, 0.5 M, 0.5 μmol). The resulting mixture was incubated at 37° C. for 30 min.

The invention claimed is:

1. A polypeptide-payload conjugate comprising:

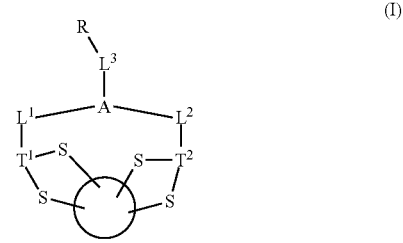

(I)

wherein the circle represents a polypeptide or polypeptide complex, which may comprise modifications other than the one shown;

each S is a sulfur atom of a cysteine residue of the polypeptide or polypeptide complex;

$T^1$ and $T^2$ each represent a tether that connects two sulfur atoms through 1-5 carbon atoms, wherein $T^1$ also attaches to $L^1$ and $T^2$ also attaches to $L^2$;

$L^1$ and $L^2$ each represent a linking group connecting $T^1$ or $T^2$, respectively, to A;

$L^3$ is a linking group that connects A to R;

A represents a group connecting $L^1$, $L^2$ and $L^3$;

and R represents a payload or a reactive functional group for attaching a payload.

2. The polypeptide-payload conjugate of claim 1, wherein the polypeptide is an antibody or an antibody Fc.

3. The polypeptide-payload conjugate of claim 2, wherein each of $T^1$ and $T^2$ comprises a chain of three carbon atoms connecting the attached sulfur atoms.

4. The polypeptide-payload conjugate of claim 1, wherein $T^1$ represents a group of the formula $CH_2-C(=N-O-[L^1])-CH_2-$, wherein $[L^1]$ indicates the point of attachment of $T^1$ to $L^1$.

5. The polypeptide-payload conjugate of claim 4, wherein $T^2$ represents a group of the formula $CH_2-C(=N-O-[L^2])-CH_2-$, wherein $[L^2]$ indicates the point of attachment of $T^2$ to $L^2$.

6. The polypeptide-payload conjugate of claim 5, wherein $L^1$ and $L^2$ are the same.

7. The polypeptide-payload conjugate of claim 6, wherein the polypeptide is an antibody or antibody Fc, and the two sulfur atoms attached to T' form a disulfide bond in the unconjugated antibody or antibody Fc.

8. The polypeptide-payload conjugate of claim 7, wherein the polypeptide is an antibody or antibody Fc, and the two sulfur atoms attached to $T^2$ form a disulfide bond in the unconjugated polypeptide.

9. The polypeptide-payload conjugate of claim 8, wherein R represents a therapeutic agent, a detectable label, an antigen, or a binding group.

10. The polypeptide-payload conjugate of claim 9, wherein R represents a cytotoxin.

11. The polypeptide-payload conjugate of claim 10, wherein A is N, CH, phenyl, $C_{3-6}$ cycloalkyl, or a 5-6 membered heterocyclic or heteroaryl group having up to two heteroatoms selected from N, O and S as ring members.

12. The polypeptide-payload conjugate of claim 11, which is of the formula

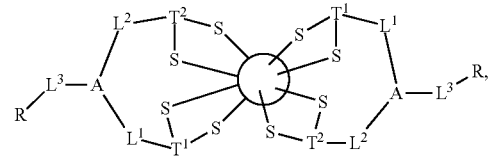

wherein the circle represents an antibody.

13. A pharmaceutical composition comprising the polypeptide-payload conjugate of claim 1 and at least one pharmaceutically acceptable carrier, diluent, or buffer.

* * * * *